United States Patent [19]

Maurer et al.

[11] 4,162,310
[45] Jul. 24, 1979

[54] COMBATING ARTHROPODS WITH O-ALKYL-O-[5-SUBSTITUTED-PYRIMIDIN(4)-YL]-(THIONO)(THIOL)-PHOSPHORIC(PHOSPHONIC)ACID ESTERS

[75] Inventors: Fritz Maurer; Hans-Jochem Riebel; Rolf Schröder, all of Wuppertal; Ingeborg Hammann, Cologne; Wolfgang Behrenz, Overath, all of Fed. Rep. of Germany

[73] Assignee: Bayer Aktiengesellschaft, Leverkusen, Fed. Rep. of Germany

[21] Appl. No.: 827,511

[22] Filed: Aug. 24, 1977

[30] Foreign Application Priority Data

Sep. 1, 1976 [DE] Fed. Rep. of Germany ....... 2639256

[51] Int. Cl.² ........................... A01N 9/36; C07F 9/65
[52] U.S. Cl. ..................... 424/200; 544/243
[58] Field of Search ............... 260/251 P; 424/200; 544/243

[56] References Cited

U.S. PATENT DOCUMENTS

| | | | |
|---|---|---|---|
| 2,754,243 | 7/1956 | Gysin et al. | 424/200 |
| 3,862,188 | 1/1975 | Milzner et al. | 260/251 P |
| 3,886,156 | 5/1975 | Hofer et al. | 260/251 P |
| 3,951,975 | 4/1976 | Hofer et al. | 260/251 P |
| 3,966,730 | 6/1976 | Hofer et al. | 260/251 P |
| 4,127,652 | 11/1978 | Maurer et al. | 424/200 |

Primary Examiner—Donald G. Daus
Assistant Examiner—Diana G. Rivers
Attorney, Agent, or Firm—Sprung, Felfe, Horn, Lynch & Kramer

[57] ABSTRACT

O-alkyl-O-[5-substituted-pyrimidin(4)yl]-(thiono)(thiol)-phosphoric (phosphonic) acid esters of the formula

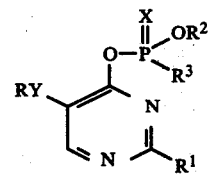

in which
  R and $R^2$ each independently is alkyl,
  $R^1$ is hydrogen or alkyl,
  $R^3$ is alkyl, alkoxy, alkylthio or phenyl, and
  X and Y each independently is oxygen or sulfur,
which possess arthropodicidal properties.

10 Claims, No Drawings

COMBATING ARTHROPODS WITH O-ALKYL-O-[5-SUBSTITUTED-PYRIMIDIN(4)-YL]-(THIONO)(THIOL)-PHOSPHORIC(PHOSPHONIC)ACID ESTERS

The present invention relates to and has for its objects the provision of particular new O-alkyl-O-[5-substituted-pyrimidin(4)yl]-(thiono)(thiol) phosphoric (phosphonic) acid esters which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from U.S. Patent Nos. 2,754,243, 3,886,156 and 3,966,730 that certain pyrimidinethionophosphoric (phosphonic) acid esters, for example O,O-diethyl-O-[2-isopropyl-6-methyl- (Compound C) or 2,5-dimethylthio-6-methylpyrimidin(4)yl]-thionophosphoric acid ester (Comound A) and O-ethyl-O-[2-isopropoxy-5-cyano-pyrimidin(4)yl]-thionoethanephosphonic acid ester (Compound D), possess insecticidal and acaricidal properties.

The present invention now provides, as new compounds, the alkoxy-substituted and alkylthio-substituted pyrimidine (thiono)(thiol)-phosphoric(phosphonic) acid esters of the general formula

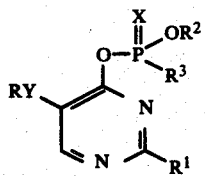

in which
R and $R^2$ each independently is alkyl,
$R^1$ is hydrogen or alkyl,
$R^3$ is alkyl, alkoxy, alkylthio or phenyl, and
X and Y each independently is oxygen or sulfur.

Preferably, R and $R^2$, which may be identical or different, each represent straight-chain or branched alkyl with 1 to 6 (especially 1 to 4) carbon atoms, $R^1$ represents straight-chain or branched alkyl with 1 to 6 (especially 1 to 4) carbon atoms, $R^3$ represents phenyl, straight-chain or branched alkyl with 1 to 4 (especially 1 to 3) carbon atoms, straight-chain or branched alkylthio with 1 to 6 (especially 1 to 4) carbon atoms or straight-chain or branched alkoxy with 1 to 4 (especially 1 to 3) carbon atoms, X represents sulphur and Y represents oxygen.

Surprisingly, the alkoxy-substituted and alkylthio-substituted pyrimidine(thiono)(thiol)-phosphoric(phosphonic) acid esters according to the invention exhibit a better insecticidal and acaricidal action than the known pyrimidinethiono-phosphoric(phosphonic) acid esters of analogous structure and of the same type of action. The compounds according to the present invention thus represent a genuine enrichment of the art.

The present invention also provides a process for the preparation of an alkoxy-substituted or alkylthio-substituted pyrimidine(thiono)(thiol)-phosphoric(phosphonic) acid ester of the formula (I), in which a (thiono)(thiol)-phosphoric(phosphonic) acid ester halide of the general formula

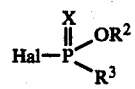

in which
$R^2$, $R^3$ and X have the above-mentioned meanings and
Hal represents halogen, preferably chlorine,
is reacted, if appropriate in the presence of a solvent or diluent, with an alkoxy-substituted or alkylthio-substituted 4-hydroxy-pyrimidine of the general formula

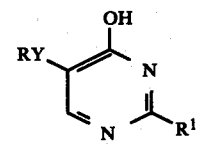

in which Y, R and $R^1$ have the above-mentioned meanings,
the latter being employed either in the form of an alkali metal salt, alkaline earth metal salt or ammonium salt or as such in the presence of an acid acceptor.

If, for example, O-iso-propyl-thionophenylphosphonic acid ester chloride and 2-ethyl-4-hydroxy-5-n-propoxypyrimidine are used as starting materials, the course of the reaction can be represented by the following equation:

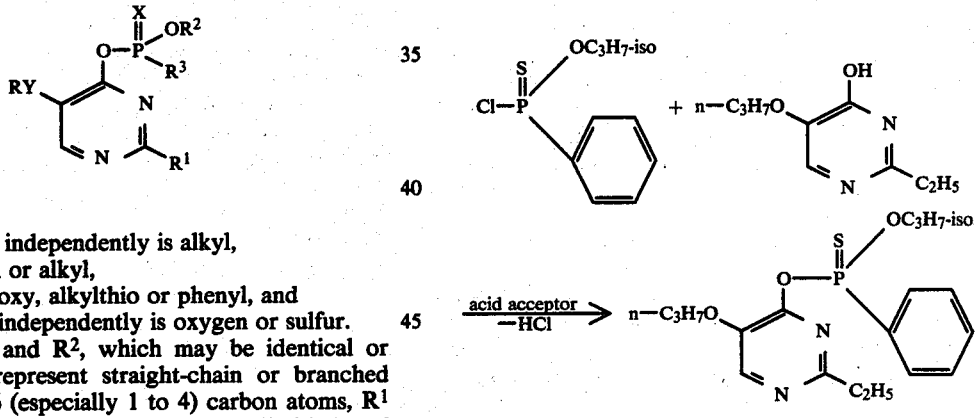

The (thiono)(thiol)-phosphoric(phosphonic) acid ester halides (II) to be used as starting materials are known and can be prepared in a simple manner in accordance with processes known from the literature. The following may be mentioned as individual examples of these compounds: O,O-dimethyl-, O,O-diethyl-, O,O-di-n-propyl-, O,O-di-isopropyl-, O,O-di-n-butyl-, O,O-di-iso-butyl-, O,O-di-sec.-butyl-, O-methyl-O-ethyl-, O-methyl-O-n-propyl-, O-methyl-O-isopropyl-, O-methyl-O-n-butyl-, O-methyl-O-iso-butyl-, O-methyl-O-sec.-butyl-, O-ethyl-O-n-propyl-, O-ethyl-O-isopropyl-, O-ethyl-O-n-butyl-, O-ethyl-O-sec.-butyl-, O-ethyl-O-iso-butyl-, O-n-propyl-O-butyl- and O-iso-propyl-O-butylthionophosphoric acid diester chloride, as well as O,S-dimethyl-, O,S-diethyl-, O,S-di-n-propyl-, O,S-di-isopropyl-, O,S-di-n-butyl-, O,S-di-iso-butyl-, O,S-di-tert.-butyl-, O,S-di-n-pentyl-, O-ethyl-S-n-propyl-, O-ethyl-S-isopropyl-, O-ethyl-S-n-butyl-, O-ethyl-S-sec.-butyl-, O-n-propyl-S-ethyl-, O-n-propyl-S-isopropyl-, O-n-butyl-S-n-propyl- and O-sec.-butyl-S-ethyl-thionothiolphosphoric acid diester chloride and O-methyl-, O-ethyl-, O-n-propyl-, O-iso-propyl-, O-n-butyl-, O-iso-butyl- and O-sec.-butylmethane-, -ethane-, -n-propane-, -iso-propane- and benzene thionophosphonic acid ester chloride.

The alkoxy-substituted or alkylthio-substituted 4-hydroxy-pyrimidines (III), also to be used as starting materials, may be synthesized from amidines and alkoxy- or alkylthio-formylacetic acid alkyl esters, if appropriate in the presence of an alcoholate.

The following may be mentioned as individual examples thereof: 5-methoxy-, 5-ethoxy-, 5-n-propoxy-, 5-iso-propoxy-, 5-n-butoxy-, 5-iso-butoxy-, 5-sec.-butoxy-, 5-methylthio-, 5-ethylthio-, 5-n-propylthio-, 5-iso-propylthio-, 5-n-butylthio-, 5-iso-butylthio-, 5-methoxy-2-methyl-, 5-ethoxy-2-methyl-, 5-n-propoxy-2-methyl-, 5-iso-propoxy-2-methyl-, 5-n-butoxy-2-methyl-, 5-iso-butoxy-2-methyl-, 5-sec.-butoxy-2-methyl-, 5-methylthio-2-methyl-, 5-ethylthio-2-methyl-, 5-n-propylthio-2-methyl-, 5-iso-propylthio-2-methyl-, 5-n-butylthio-2-methyl-, 5-iso-butylthio-2-methyl-, 5-methoxy-2-ethyl-, 5-ethoxy-2-ethyl-, 5-n-propoxy-2-ethyl-, 5-iso-propoxy-2-ethyl-, 5-n-butoxy-2-ethyl-, 5-iso-butoxy-2-ethyl-, 5-sec.-butoxy-2-ethyl-, 5-methyl-thio-2-ethyl-, 5-ethylthio-2-ethyl-, 5-n-propylthio-2-ethyl-, 5-iso-propylthio-2-ethyl-, 5-n-butylthio-2-ethyl-, 5-iso-butylthio-2-ethyl-, 5-methoxy-2-n-propyl-, 5-ethoxy-2-n-propyl-, 5-n-propoxy-2-n-propyl-, 5-iso-propoxy-2-n-propyl-, 5-n-butoxy-2-n-propyl-, 5-iso-butoxy-2-n-propyl-, 5-sec.-butoxy-2-n-propyl-, 5-methylthio-2-n-propyl-, 5-ethylthio-2-n-propyl-, 5-n-propylthio-2-n-propyl-, 5-iso-propylthio-2-n-propyl-, 5-n-butylthio-2-n-propyl-, 5-iso-butylthio-2-n-propyl-, 5-methoxy-2-iso-propyl-, 5-ethoxy-2-iso-propyl-, 5-n-propoxy-2-iso-propyl-, 5-iso-propoxy-2-iso-propyl-, 5-n-butoxy-2-iso-propyl-, 5-iso-butoxy-2-iso-propyl-, 5-sec.-butoxy-2-iso-propyl-, 5-methylthio-2-iso-propyl-, 5-ethylthio-2-iso-propyl-, 5-n-propylthio-2-iso-propyl-, 5-iso-propylthio-2-iso-propyl-, 5-n-butylthio-2-iso-propyl-, 5-iso-butylthio-2-iso-propyl-, 5-methoxy-2-n-butyl-, 5-ethoxy-2-n-butyl-, 5-n-propoxy-2-n-butyl-, 5-iso-propoxy-2-n-butyl-, 5-n-butoxy-2-n-butyl-, 5-sec.-butoxy-2-n-butyl-, 5-methylthio-2-n-butyl-, 5-ethylthio-2-n-butyl-, 5-n-propylthio-2-n-butyl-, 5-iso-propylthio-2-n-butyl-, 5-n-butylthio-2-n-butyl-, 5-iso-butylthio-2-n-butyl-, 5-methoxy-2-iso-butyl-, 5-ethoxy-2-iso-butyl-, 5-n-propoxy-2-iso-butyl-, 5-iso-propoxy-2-iso-butyl-, 5-n-butoxy-2-iso-butyl-, 5-iso-butoxy-2-iso-butyl-, 5-sec.-butoxy-2-iso-butyl-, 5-methylthio-2-iso-butyl-, 5-ethylthio-2-iso-butyl-, 5-n-propylthio-2-iso-butyl-, 5-iso-propylthio-2-iso-butyl-, 5-n-butylthio-2-iso-butyl-, 5-iso-butylthio-2-iso-butyl-, 5-methoxy-2-sec.-butyl-, 5-ethoxy-2-sec.-butyl-, 5-n-propoxy-2-sec.-butyl-, 5-iso-propoxy-2-sec.-butyl-, 5-n-butoxy-2-sec.-butyl-, 5-iso-butoxy-2-sec.-butyl-, 5-sec.-butoxy-2-sec.-butyl-, 5-methylthio-2-sec.-butyl-, 5-ethylthio-2-sec.-butyl-, 5-n-propylthio-2-sec.-butyl-, 5-iso-propylthio-2-sec.-butyl-, 5-n-butylthio-2-sec.-butyl-, 5-iso-butylthio-2-sec.-butyl-, 5-methoxy-2-tert.-butyl-, 5-ethoxy-2-tert.-butyl-, 5-iso-propoxy-2-tert.-butyl, 5-n-butoxy-2-tert.-butyl-, 5-iso-butoxy-2-tert.-butyl-, 5-sec.-butoxy-2-tert.-butyl-, 5-methylthio-2-tert.-butyl-, 5-ethylthio-2-tert.-butyl-, 5-n-propylthio-2-tert.-butyl-, 5-iso-propylthio-2-tert.-butyl-, 5-n-butylthio-2-tert.-butyl- and 5-iso-butylthio-2-tert.-butyl-4-hydroxypyrimidine.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxanes; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 0° to 120° C., preferably at from 10° to 55° C.

In general, the reaction is allowed to take place under normal pressure.

To carry out the process, the starting materials are preferably employed in equimolar amounts. An excess of one or other reactant produces no significant advantages.

In general, the reactants are combined in one of the stated solvents and are stirred for one or more hours, in most cases at an elevated temperature, to complete the reaction. After cooling, an organic solvent, for example toluene, is added to the mixture and the organic phase is worked up in the usual manner by washing, drying, and distilling off the solvent.

The new compounds are frequently obtained in the form of oils, which in most cases cannot be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine, since they are also active against animal parasites, in particular ectoparasites such as parasitic fly larvae.

The active compounds are well tolerated by plants, have a favorable level of toxicity to warm-blooded animals, and can be used for combating arthropod pests, especially insects and arachnid, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

From the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capus reticulana, Choristoneura fumiferana, Clysis ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophilia melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus Oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsions concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), haloogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.), as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as higher-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as nonionic and/or anionic emulsifying agents (e.g. polyethylene oxide esters of fatty acids, polyethylene oxide ethers of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.1–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplated methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compound of the present invention are illustrated, without limitation, by the following examples:

EXAMPLE 1:

(a) The 4-hydroxy-pyrimidines (III) required as starting materials could be prepared, for example, as follows:

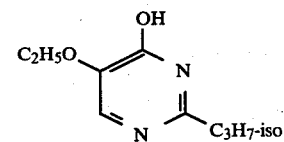

A suspension of 21.6 g (0.4 mol) of sodium methylate, 24.5 g (0.2 mol) of iso-butylamidine hydrochloride and 32 g (0.2 mol) of formylethoxyacetic acid ethyl ester was heated for 6 hours under reflux. The mixture was then evaporated and the residue was taken up in 200 ml of water. Concentrated hydrochloric acid was added to the aqueous phase, while cooling with ice, to a pH of about 6, and the mixture was then extracted twice with 200 ml of methylene chloride each time. The combined methylene chloride extracts were dried over sodium sulphate and then concentrated. 22 g (60.5% of theory)

of 2-isopropyl-5-ethoxy-4-hydroxy-pyrimidine were obtained in the form of colorless crystals of melting point 154° C.

The following starting materials could be synthesis analogously:

Table 1

| Structure | Yield (% of theory) | Melting point (°C.) |
|---|---|---|
| iso-C₃H₇O-...-C₃H₇-iso (OH, N, N) | 56 | 108–109 |
| CH₃S-...-C₃H₇-iso (OH, N, N) | 49 | 175 |
| CH₃S-...-CH₃ (OH, N, N) | 99 | >220 |
| C₂H₅O-...-CH₃ (OH, N, N) | 61 | 160 |
| CH₃O-...-C₃H₇-iso (OH, N, N) | 65 | 167 |
| CH₃O-...-CH₃ (OH, N, N) | 51 | 206 |
| C₂H₅O-...-CH₃ (OH, N, N) | 37 | — |

Table 1-continued

| Structure | Yield (% of theory) | Melting point (°C.) |
|---|---|---|
| CH₃O-...-C₂H₅ (OH, N, N) | 65 | — |
| C₂H₅O-...-(pyrimidine) (OH, N, N) | 45 | 137 | b) 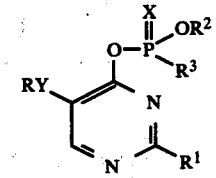 (1)

18.8 g (0.1 mol) of O,O-diethylthionophosphoric acid diester chloride were added dropwise to a suspension of 18.2 g (0.1 mol) of 2-isopropyl-4-hydroxy-5-ethoxy-pyrimidine, 14.5 g (0.105 mol) of potassium carbonate and 200 ml of acetonitrile at 20° C. The reaction mixture was heated to 40° C. for 3 hours, cooled and poured into 300 ml of toluene. The toluene solution was washed with saturated sodium bicarbonate solution and water and dried over sodium sulphate and then concentrated. After slight distillation, 13 g (39% of theory) of O,O-diethyl-O-[2-isopropyl-5-ethoxy-pyrimidin(4)yl]-thionophosphoric acid ester were obtained in the form of a yellow oil having a refractive index $n_D^{23}$ of 1.4960.

The following compounds of the formula $$\begin{array}{c} \text{RY} \\ \text{O-P(=X)(OR}^2\text{)R}^3 \\ \text{N=...R}^1 \end{array} \quad (I)$$

could be synthesized analogously:

Table 2

| Example No. | R | R¹ | R² | R³ | X | Y | Yield (% of theory) | Refractive index: |
|---|---|---|---|---|---|---|---|---|
| 2 | C₂H₅ | C₃H₇-iso | C₂H₅ | C₃H₇S | S | O | 26 | $n_D^{23}$:1.5269 |
| 3 | C₂H₅ | C₃H₇-iso | C₂H₅ | C₂H₅ | S | O | 41 | $n_D^{23}$:1.5071 |
| 4 | C₂H₅ | C₃H₇-iso | CH₃ | OCH₃ | S | O | 30 | $n_D^{20}$:1.5160 |
| 5 | C₂H₅ | C₃H₇-iso | C₂H₅ | OC₂H₅ | O | O | 54 | $n_D^{20}$:1.4746 |
| 6 | C₂H₅ | C₃H₇-iso | C₃H₇-iso | CH₃ | S | O | 88 | $n_D^{20}$:1.5030 |
| 7 | C₂H₅ | C₃H₇-iso | CH₃ | C₂H₅ | S | O | 99 | $n_D^{20}$:1.5170 |
| 8 | C₂H₅ | C₃H₇-iso | C₄H₉-iso | C₂H₅ | S | O | 69 | $n_D^{20}$:1,4983 |
| 9 | C₃H₇-iso | C₃H₇-iso | C₂H₅ | OC₂H₅ | S | O | 54 | $n_D^{24}$:1.4928 |
| 10 | C₃H₇-iso | C₃H₇-iso | C₂H₅ | C₂H₅ | S | O | 68 | $n_D^{24}$:1.5019 |
| 11 | C₃H₇-iso | C₃H₇-iso | C₄H₉-iso | C₂H₅ | S | O | 70 | $n_D^{24}$:1.4925 |

| Compound No. | R | R¹ | R² | R³ | X | Y | Yield (% of theory) | Refractive index: |
|---|---|---|---|---|---|---|---|---|
| 12 | CH₃ | CH₃ | C₂H₅ | OC₂H₅ | S | S | 38 | $n_D^{22}$:1.5358 |
| 13 | CH₃ | CH₃ | C₂H₅ | C₂H₅ | S | S | 47 | $n_D^{22}$:1.5480 |
| 14 | CH₃ | C₃H₇-iso | C₂H₅ | OC₂H₅ | S | S | 45 | $n_D^{22}$:1.5258 |
| 15 | CH₃ | C₃H₇-iso | C₂H₅ | C₂H₅ | S | S | 66 | $n_D^{22}$:1.5380 |
| 16 | CH₃ | C₃H₇-iso | C₃H₇-iso | CH₃ | S | S | 63 | $n_D^{22}$:1.5342 |
| 17 | CH₃ | C₃H₇-iso | C₂H₅ | CH₃ | S | S | 77 | $n_D^{22}$:1.5443 |

Table 2-continued

| | | | | | | | | |
|---|---|---|---|---|---|---|---|---|
| 18 | C$_2$H$_5$ | CH$_3$ | C$_2$H$_5$ | OC$_2$H$_5$ | O | O | 17 | n$_D^{22}$:1.4682 |
| 19 | C$_2$H$_5$ | CH$_3$ | C$_2$H$_5$ | OC$_2$H$_5$ | S | O | 21 | n$_D^{22}$:1.4981 |
| 20 | C$_2$H$_5$ | CH$_3$ | C$_2$H$_5$ | C$_2$H$_5$ | S | O | 76 | n$_D^{22}$:1.5152 |
| 21 | CH$_3$ | C$_3$H$_7$-iso | C$_2$H$_5$ | C$_2$H$_5$ | S | O | 83 | n$_D^{22}$:1.5122 |
| 22 | CH$_3$ | C$_3$H$_7$-iso | C$_2$H$_5$ | OC$_2$H$_5$ | S | O | 76 | n$_D^{22}$:1.5011 |
| 23 | CH$_3$ | C$_3$H$_7$-iso | CH$_3$ | C$_2$H$_5$ | S | O | 87 | n$_D^{21}$:1.5196 |
| 24 | CH$_3$ | C$_3$H$_7$-iso | CH$_3$ | OCH$_3$ | S | O | 34 | n$_D^{22}$:1.5268 |
| 25 | CH$_3$ | C$_3$H$_7$-iso | C$_3$H$_7$-iso | CH$_3$ | S | O | 92 | n$_D^{21}$:1.5099 |
| 26 | CH$_3$ | C$_3$H$_7$-iso | C$_2$H$_5$ | OC$_2$H$_5$ | O | O | 50 | n$_D^{22}$:1.4673 |
| 27 | C$_2$H$_5$ | CH$_3$ | C$_2$H$_5$ | OC$_2$H$_5$ | S | O | 70 | n$_D^{20}$:1.5027 |
| 28 | C$_2$H$_5$ | CH$_3$ | C$_2$H$_5$ | SC$_3$H$_7$-n | S | O | 65 | n$_D^{20}$:1.5282 |
| 29 | CH$_3$ | C$_2$H$_5$ | C$_2$H$_5$ | OC$_2$H$_5$ | S | O | 81 | n$_D^{20}$:1.4990 |
| 30 | CH$_3$ | C$_2$H$_5$ | C$_2$H$_5$ | C$_2$H$_5$ | S | O | 85 | n$_D^{22}$:1.5157 |
| 31 | CH$_3$ | C$_2$H$_5$ | C$_2$H$_5$ | 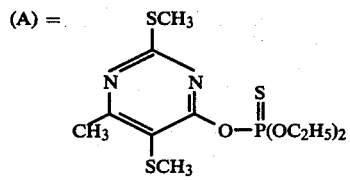 | S | O | 73 | n$_D^{22}$:1.5623 |
| 32 | CH$_3$ | CH$_3$ | C$_2$H$_5$ | C$_2$H$_5$ | S | O | 80 | n$_D^{22}$:1.5244 |
| 33 | CH$_3$ | CH$_3$ | C$_2$H$_5$ | OC$_2$H$_5$ | S | O | 59 | n$_D^{22}$:1.5075 |
| 34 | CH$_3$ | CH$_3$ | C$_3$H$_7$-iso | C$_2$H$_5$ | S | O | 85 | n$_D^{22}$:1.5138 |
| 35 | CH$_3$ | CH$_3$ | C$_2$H$_5$ | 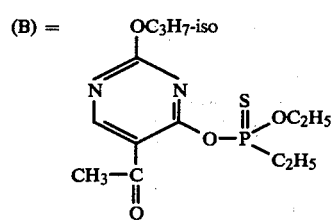 | S | O | 57 | n$_D^{22}$:1.5732 |
| 36 | CH$_3$ | C$_2$H$_5$ | C$_3$H$_7$-iso | CH$_3$ | S | O | 90 | n$_D^{22}$:1.5140 |
| 37 | CH$_3$ | C$_2$H$_5$ | C$_3$H$_7$-iso | C$_2$H$_5$ | S | O | 88 | n$_D^{22}$:1.5095 |
| 38 | CH$_3$ | C$_2$H$_5$ | C$_2$H$_5$ | SC$_3$H$_7$-n | S | O | 60 | n$_D^{22}$:1.5319 |
| 39 | C$_2$H$_5$ | CH$_3$ | C$_3$H$_7$-iso | CH$_3$ | S | O | 80 | 57° C. (m.pt) |
| 40 | C$_2$H$_5$ | CH$_3$ | C$_3$H$_7$-iso | C$_2$H$_5$ | S | O | 88 | n$_D^{22}$:1.5067 |
| 41 | C$_2$H$_5$ | CH$_3$ | C$_2$H$_5$ | 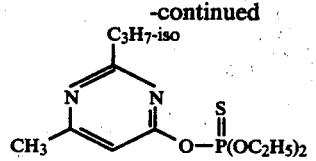 | S | O | 79 | n$_D^{22}$:1.5641 |
| 42 | CH$_3$ | C$_3$H$_7$-iso | CH$_3$ | CH$_3$ | S | O | 35 | n$_D^{25}$:1.5191 |
| 43 | CH$_3$ | CH$_3$ | C$_2$H$_5$ | OC$_2$H$_5$ | O | O | 47 | n$_D^{22}$:1.4778 |
| 44 | CH$_3$ | CH$_3$ | CH$_3$ | C$_2$H$_5$ | S | O | 69 | 41° C. (m.pt) |
| 45 | CH$_3$ | CH$_3$ | C$_2$H$_5$ | CH$_3$ | S | O | 69 | n$_D^{23}$:1.5262 |
| 46 | CH$_3$ | CH$_3$ | C$_3$H$_7$-iso | CH$_3$ | S | O | 69 | n$_D^{23}$:1.5160 |
| 47 | CH$_3$ | CH$_3$ | CH$_3$ | CH$_3$ | S | O | | |
| 48 | CH$_3$ | C$_2$H$_5$ | C$_2$H$_5$ | OC$_2$H$_5$ | O | O | 55 | n$_D^{22}$:1.4775 |
| 49 | CH$_3$ | C$_2$H$_5$ | CH$_3$ | CH$_3$ | S | O | | |
| 50 | C$_2$H$_5$ | H | C$_2$H$_5$ | C$_2$H$_5$ | S | O | 80 | n$_D^{23}$:1.5197 |
| 51 | C$_2$H$_5$ | H | C$_2$H$_5$ | CH$_3$ | S | O | 84 | n$_D^{23}$:1.5264 |
| 52 | C$_2$H$_5$ | H | C$_3$H$_7$-iso | CH$_3$ | S | O | 87 | n$_D^{23}$:1.5159 |
| 53 | C$_2$H$_5$ | H | CH$_3$ | C$_2$H$_5$ | S | O | 69 | n$_D^{23}$:1.5320 |
| 54 | C$_2$H$_5$ | C$_3$H$_7$-iso | C$_2$H$_5$ | 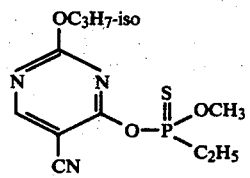 | S | O | 52 | n$_D^{24}$:1.5590 |
| 55 | CH$_3$ | CH$_3$ | C$_2$H$_5$ |  | S | S | 38 | n$_D^{24}$:1.6120 |

The insecticidal and acaricidal activity of the compounds of this invention is illustrated by the following examples wherein the compounds according to the present invention are each identified by the number (given in brackets) from the preparative examples, while the known comparison compounds are identified as follows:

(A) = 

(B) = 

(C) = 

(D) =

EXAMPLE 2

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% meant that all of the caterpillars were killed whereas 0% meant that none of the caterpillars were killed.

The active compounds, the concentrations of the active compounds, the evaluation times and the results can be seen from the following table:

Table 3

| Active compound | (Plutella test) Active compound concentration in % | Degree of destruction in % after 3 days |
|---|---|---|
| (A) | 0.1 | 80 |
|  | 0.01 | 0 |
| (B) | 0.1 | 100 |
|  | 0.01 | 0 |
| (50) | 0.1 | 100 |
|  | 0.01 | 100 |
| (51) | 0.1 | 100 |
|  | 0.01 | 100 |
| (52) | 0.1 | 100 |
|  | 0.01 | 100 |
| (33) | 0.1 | 100 |
|  | 0.01 | 100 |
| (32) | 0.1 | 100 |
|  | 0.01 | 100 |
| (13) | 0.1 | 100 |
|  | 0.01 | 100 |
| (18) | 0.1 | 100 |
|  | 0.01 | 100 |
| (19) | 0.1 | 100 |
|  | 0.01 | 100 |
| (28) | 0.1 | 100 |
|  | 0.01 | 100 |
| (29) | 0.1 | 100 |
|  | 0.01 | 100 |
| (30) | 0.1 | 100 |
|  | 0.01 | 100 |
| (36) | 0.1 | 100 |
|  | 0.01 | 100 |
| (37) | 0.1 | 100 |
|  | 0.01 | 100 |
| (38) | 0.1 | 100 |
|  | 0.01 | 100 |
| (31) | 0.1 | 100 |
|  | 0.01 | 100 |
| (24) | 0.1 | 100 |
|  | 0.01 | 100 |
| (42) | 0.1 | 100 |
|  | 0.01 | 100 |
| (23) | 0.1 | 100 |
|  | 0.01 | 100 |
| (25) | 0.1 | 100 |
|  | 0.01 | 100 |
| (22) | 0.1 | 100 |
|  | 0.01 | 100 |
| (21) | 0.1 | 100 |
|  | 0.01 | 100 |
| (26) | 0.1 | 100 |
|  | 0.01 | 100 |
| (14) | 0.1 | 100 |
|  | 0.01 | 100 |
| (15) | 0.1 | 100 |
|  | 0.01 | 100 |
| (17) | 0.1 | 100 |
|  | 0.01 | 100 |
| (16) | 0.1 | 100 |
|  | 0.01 | 100 |
| (4) | 0.1 | 100 |
|  | 0.01 | 100 |
| (7) | 0.1 | 100 |
|  | 0.01 | 100 |
| (1) | 0.1 | 100 |
|  | 0.01 | 100 |
| (3) | 0.1 | 100 |

Table 3-continued

| Active compound | (Plutella test) Active compound concentration in % | Degree of destruction in % after 3 days |
|---|---|---|
|  | 0.01 | 100 |
| (5) | 0.1 | 100 |
|  | 0.01 | 100 |
| (6) | 0.1 | 100 |
|  | 0.01 | 100 |
| (2) | 0.1 | 100 |
|  | 0.01 | 100 |
| (8) | 0.1 | 100 |
|  | 0.01 | 100 |
| (9) | 0.1 | 100 |
|  | 0.01 | 100 |
| (10) | 0.1 | 100 |
|  | 0.01 | 100 |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 4

| Active compound | (Tetranychus test) Active compound concentration in % | Degree of destruction in % after 2 days |
|---|---|---|
| (A) | 0.1 | 0 |
| (C) | 0.1 | 95 |
|  | 0.01 | 0 |
| (B) | 0.1 | 20 |
|  | 0.01 | 0 |
| (D) | 0.1 | 50 |
|  | 0.01 | 0 |
| (53) | 0.1 | 100 |
|  | 0.01 | 100 |
| (32) | 0.1 | 100 |
|  | 0.01 | 98 |
| (34) | 0.1 | 100 |
|  | 0.01 | 80 |
| (35) | 0.1 | 99 |
|  | 0.01 | 95 |
| (18) | 0.1 | 99 |
|  | 0.01 | 80 |
| (30) | 0.1 | 100 |
|  | 0.01 | 100 |
| (25) | 0.1 | 100 |
|  | 0.01 | 90 |

EXAMPLE 4

LT$_{100}$ test for Diptera

Test insects: *Aëdes aegypti.*
Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the active compounds and the times at which there was 100% destruction can be seen from the following table:

Table 5

| (LT$_{100}$ test for *Diptera/Aëdes aegypti*) | |
|---|---|
| Active compound | Active compound concentration of the solution in % | LT$_{100}$ in minutes (') or hours (h) |

| Active compound | Active compound concentration of the solution in % | LT$_{100}$ in minutes (') or hours (h) |
|---|---|---|
| (A) | 0.02 | 3 h = 0% |
| (21) | 0.02 | 120' |
| (22) | 0.02 | 120' |
| (23) | 0.02 | 120' |
| (32) | 0.02 | 60' |
| (34) | 0.02 | 60' |
| (36) | 0.02 | 60' |
| (37) | 0.02 | 60' |
| (39) | 0.02 | 120' |
| (40) | 0.02 | 120' |
| (1) | 0.02 | 120' |
| (3) | 0.02 | 60' |
| (18) | 0.02 | 120' |
| (19) | 0.02 | 120' |
| (20) | 0.02 | 120' |
| (50) | 0.02 | 60' |

EXAMPLE 5

Test insects: *Sitophilus granarius*
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all of the test insects had been killed; 0% denoted that none of the test insects had been killed.

The active compounds, the concentrations of the active compounds, and the results can be seen from the following table:

Table 6

| (*Sitophilus granarius*) | | |
|---|---|---|
| Active compound | Active compound concentration of the solution in % | Degree of destruction in % |
| (D) | 0.02 | 0 |
| (25) | 0.02 | 100 |
| (24) | 0.02 | 100 |
| (26) | 0.02 | 100 |
| (29) | 0.02 | 100 |
| (30) | 0.02 | 100 |
| (31) | 0.02 | 100 |
| (33) | 0.02 | 100 |
| (35) | 0.02 | 100 |
| (38) | 0.02 | 100 |
| (41) | 0.02 | 100 |
| (2) | 0.02 | 90 |
| (5) | 0.02 | 100 |
| (6) | 0.02 | 100 |
| (7) | 0.02 | 100 |
| (8) | 0.02 | 100 |
| (9) | 0.02 | 100 |
| (10) | 0.02 | 100 |
| (11) | 0.02 | 100 |
| (13) | 0.02 | 90 |
| (52) | 0.02 | 100 |

It will be appreciated that the instant specification and examples are set forth by way of illustration and not limitation, and that various modifications and changes may be made without departing from the spirit and scope of the present invention.

What is claimed is:

1. An O-alkyl-O-[5-substituted-pyrimidin (4)yl]-(thiono) (thiol)-phosphoric (phosphonic acid ester of the formula

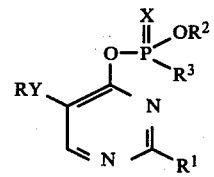

in which
R and R$^2$ each independently is alkyl with 1 to 6 carbon atoms,
R$^1$ is hydrogen or alkyl with 1 to 6 carbon atoms,
R$^3$ is alkyl with 1 to 4 carbon atoms, alkoxy with 1 to 4 carbons atoms, alkylthio with 1 to 6 carbon atoms, or phenyl, and
X and Y each independently is oxygen or sulphur.

2. A compound according to claim 1, in which
X is sulphur, and
Y is oxygen.

3. A compound according to claim 1 wherein such compound is O-ethyl-O-[2-isopropyl-5-ethoxy-pyrimidin(4)yl]-ethane-thionophosphonic acid ester of the formula

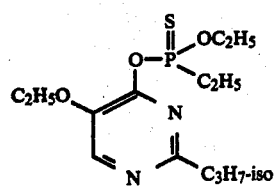

4. A compound according to claim 1 wherein such compound is O-methyl-O-[2-isopropyl-5-ethoxy-pyrimidin(4)yl]-ethane-thionophosphonic acid ester of the formula

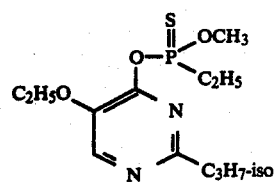

5. A compound according to claim 1 wherein such compound is O,O-diethyl-O-[2-isopropyl-5-methoxy-pyrimidin(4)yl]-thionophosphoric acid ester of the formula

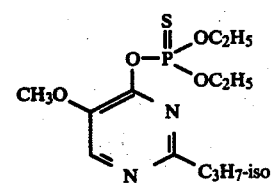

6. A compound according to claim 1 wherein such compound is O-methyl-O-[2-methyl-5-methoxy-pyrimidin(4)yl]-ethane-thionophosphonic acid ester of the formula 7. A compound according to claim 1 wherein such compound is O-ethyl-O-[2-methyl-5-methoxy-pyrimidin(4)yl]-methane-thionophosphonic acid ester of the formula

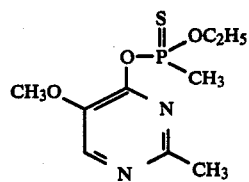

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9 in which said compound is
O-ethyl-O-[2-isopropyl-5-ethoxy-pyrimidin(4)yl]-ethane-thionophosphonic acid ester,
O-methyl-O-[2-isopropyl-5-ethoxy-pyrimidin(4)yl]-ethane-thionophosphonic acid ester,
O,O-diethyl-O-[2-isopropyl-5-methoxy-pyrimidin(4)yl]-thionophosphoric acid ester,
O-methyl-O-[2-methyl-5-methoxy-pyrimidin(4)yl]-ethane-thionophosphonic acid ester, or
O-ethyl-O-[2-methyl-5-methoxy-pyrimidin(4)yl]-methane-thionophosphonic acid ester.

* * * * *